United States Patent

Hiltawsky et al.

[11] Patent Number: 5,622,678
[45] Date of Patent: Apr. 22, 1997

[54] HIGH PRESSURE GENERATING APPARATUS

[75] Inventors: Josef Hiltawsky, Schwerte; Jörg-Peter Körner; Heribert Dierkes, both of Hagen; Hans-Ottomar Kurtz, Dortmund, all of Germany

[73] Assignee: Uhde GmbH, Dortmund, Germany

[21] Appl. No.: 448,936

[22] Filed: May 24, 1995

[30] Foreign Application Priority Data

Jun. 17, 1994 [DE] Germany .................... 44 21 341.7

[51] Int. Cl.$^6$ ............................. A61L 2/00; A23L 3/015
[52] U.S. Cl. ..................... 422/295; 422/292; 99/467; 99/485
[58] Field of Search .................. 422/295, 292; 99/467, 473, 485

[56] References Cited

U.S. PATENT DOCUMENTS

| | | | |
|---|---|---|---|
| 5,019,114 | 5/1991 | Gronbaek | 72/467 |
| 5,165,325 | 11/1992 | Akatsu | 99/485 |
| 5,213,029 | 5/1993 | Yutaka | 422/295 |
| 5,316,745 | 5/1994 | Ting et al. | 422/295 |
| 5,328,703 | 7/1994 | Nakagawa et al. | 426/52 |
| 5,370,043 | 12/1994 | Träff et al. | 99/467 |
| 5,470,547 | 11/1995 | Lhenry | 422/295 |

Primary Examiner—Robert J. Warden
Assistant Examiner—Theresa T. Snider
Attorney, Agent, or Firm—Anderson, Kill & Olick

[57] ABSTRACT

A high-pressure generating apparatus including a high-pressure chamber, a low-pressure chamber located beneath the high-pressure chamber and having a diameter substantially larger than the diameter of the high-pressure chamber, a tandem piston having first and second portions displaceable in the high-pressure and low-pressure chambers, respectively, for building-up pressure therein, and a yoke embracing the high-pressure and low-pressure chambers for applying a pressure force to the high-pressure chamber cover and the low-pressure chamber bottom upon built-up of pressure in the high pressure and low-pressure chambers.

5 Claims, 3 Drawing Sheets

HIGH PRESSURE GENERATING APPARATUS

BACKGROUND OF THE INVENTION

The present invention relates to a high pressure generating apparatus and, in particular, to an apparatus for generating high pressure required in sterilization processes. Such an apparatus includes a high-pressure chamber, forming the operating chamber, and a low-pressure chamber of a fairly large diameter, with the pressure built-up in both pressure chambers being provided by a tandem piston with different surface area size portions. The piston assembly acts as a pressure intensifier and is actuated by an externally generated hydraulic pressure applied to its large surface. The small surface generates the operating pressure in the high-pressure chamber which is arranged above the low-pressure chamber with regard to the direction of action of a gravity force, and is sealed with an upper cover. An apparatus of this type is described in EP-A-0 480 422.

Research scientists in the field of high-pressure applications discovered that isostatic pressures in the range of 500 to 10,000 bar destroy microorganisms an room temperature.

The journal "FOOD MANUFACTURE" of November 1992 published an article by Bart Mertens entitled "Under pressure", which reported that the sterilizing effect of a high pressure at room temperature had recently been utilized in the food industry.

It is mainly fruit yoghurts, jellies, salad dressings and fruit sauces, as well as citrus fruit juices, that are produced by isostatic high-pressure sterilization processes.

The food is already in its sealed package when it is subjected to isostatic high-pressure sterilization. The most suitable packaging materials for this treatment are elastomeric plastic film and aluminum foil or sheeting combining these materials. When subjected to high pressure, these materials retain their flexibility or plasticity and adjust to the compacted content and the empty part of the package. For example, the original volume of a package with contents is reduced by about 12% when such a package is subjected to sterilization at a isostatic pressure of 4,000 bar from all sides. The package is not damaged during this process.

High-pressure sterilization autoclaves for use in the food industry must, when viewed from economical point of view, allow short cycles for the feed and discharge of the products treated. The isostatic pressure must be built up within a minimum of time and be maintained on the preset level during entire compacting cycle.

EP-A-0 480 422, which has already been referred to at the beginning, describes a sterilization method for the preservation of fruit juices using high pressure. In this process, the fruit juice to be sterilized is subjected to high pressure either without packaging or in a sealed package. The pressures applied are in a range of 2,000 bar to 10,000 bar, with the treatment cycles ranging from 5 to 120 minutes. The treatment pressure and time are optimized to suit the product involved.

The fruit juice to be treated without packaging is poured directly into the high-pressure chamber. One end of the high-pressure chamber is closed with a piston, the other end is closed with a cover. The piston is actuated by a hydraulic cylinder.

For high-pressure treatment of the fruit juice in the chamber, the hydraulic cylinder presses the piston toward the cover.

Each time the piston is moved, an equilibrium of forces is created which, on the one hand, are generated by the treatment pressure acting on the surface of the autoclave piston and, on the other hand, by the hydraulic pressure acting on the surface of the actuator piston. If the hydraulic pressure is increased, the high-pressure piston penetrates into the high-pressure chamber and thus increases the pressure to which the fruit juice is subjected.

The surface of the actuator piston is larger by a multiple than that of the autoclave piston in the high-pressure chamber. For this reason, it is possible to build up a treatment pressure in the high pressure chamber amounting to a multiple of the surface pressure by means of a comparatively low hydrostatic pressure. Such a system is referred to as a pressure intensifier in high-pressure technology.

When the content of sealed packages is sterilized in the high-pressure chamber of the pressure intensifier, the pressure-transmitting fluid covers the package on all sides.

The high-pressure chamber is completely filled with the pressure transmitting fluid. The pressure required for the treatment in this chamber is generated by the piston motion. The pressurized fluid acts on the sealed packages from all sides in the high-pressure chamber.

In a publication "Application of High Pressure and Thermo-physical Properties of Water to Biotechnology" in the journal "Fluid Phase Equilibria", Volume 76, (1992), pp. 87–95, T. Makita refers to the fact that water at a temperature of 20° C. passes into a solid state (Ice VI), if subjected to a pressure of 8,840 bar. If water is used as the pressure transmitting fluid, an irreversible ice-VI formation may occur in high-pressure piping with a small cross-section if the high-pressure chamber and the pressure-generating unit are housed separately and connected via a pipeline. The ice-VI formation will cause disturbances during the operating cycle in the high-pressure chamber when feeding, treatment and discharge form an overall cycle.

A book "HIGH PRESSURE TECHNOLOGY, VOLUME I, Equipment Design, Materials and Properties," by Ian L. Spain and Jac Paauwe, 1977, published by MARCEL DEKKER, Inc., New York, USA, describes pressure intensifiers, on pages 162 to 167, and shows sketches of different stages of their operation. In the case of these pressure intensifiers, the pressure acting on the cover of the high-pressure chamber is absorbed by the cylindrical wall of the high-pressure chamber. This also generates an axial load in the cylindrical wall.

This axial force causes a triaxial state of stress in the wall material. The thickness of the cylindrical wall of the high-pressure chamber exposed to this triaxial state of stress must therefore exceed that of a wall exposed to a biaxial state of stress that generates no radial load. A thicker wall involves higher costs.

The pressure intensifiers referred to by Spain/Paauwe only permit a limited access to the high-pressure chamber. The full cross-section of the high-pressure chamber becomes accessible only after removal of the cover. However, the cover is positively connected to the cylindrical wall of the high-pressure chamber in order to ensure that the wall can withstand the force exerted by the cover.

The connecting elements have to be unscrewed in order to remove the cover, or the complete cover—in the form of a threaded plug—has to be unscrewed and removed form the opening. Economical cyclic operation, i.e. short cycles, cannot be expected of a high-pressure chamber which is provided with such a cover generating axial loads in which sealed packages are treated.

Problems associated with the use of high-pressure intensifiers are discussed to DE-C-30 32 430. DE-C-39 33 076 describes a forging press which has a stationary frame for suspending the upper die and supporting the lower die.

The object of the present invention is to provide a simple and, if possible, fully-automatic sterilization process that permits to retain the advantages of known solutions.

SUMMARY OF THE INVENTION

The object of the invention is achieved by providing an apparatus in which both pressure chambers are embraced by a movable yoke in such a manner that the cover of the high-pressure chamber and the bottom of the low-pressure chamber press against the inner surface of the yoke when the operating pressure is built up.

The embodiment of the invention permits a comparatively simple design of the pressure chamber, quick and easy opening and closing of the pressure chamber and, consequently, providing short operating cycles.

Advantageous embodiments of the inventive apparatus are described below.

Advantageously, there is provided a support for the apparatus in the form of a spring suspension in a frame, thus allowing any minor dimensional changes to be absorbed via the short spring excursion during pressure built-up or reduction.

The yoke is supported by rails. This also serves to permit semi-automatic or fully-automatic movement, for instance, in such a manner that the yoke is moved on the rails by hydraulic cylinders.

A particularly advantageous embodiment of the invention contemplates providing several cylindrical sections forming the cylinder wall of the high-pressure chamber, an inner liner and a number of ring members formed of metal tape which embraces this inner liner.

Such ring members are per se already known, for instance, from DE-A-38 34 996. These ring member are, for instance, used as part of die forging tools. The present invention makes use of this technology and provides for a similar design of the walls of the high-pressure vessels.

BRIEF DESCRIPTION OF THE DRAWINGS

The present invention will now be explained in more detail with reference to the accompanying drawings, wherein.

DETAILED DESCRIPTION OF THE PREFERRED EMBODIMENT

Figure 1:
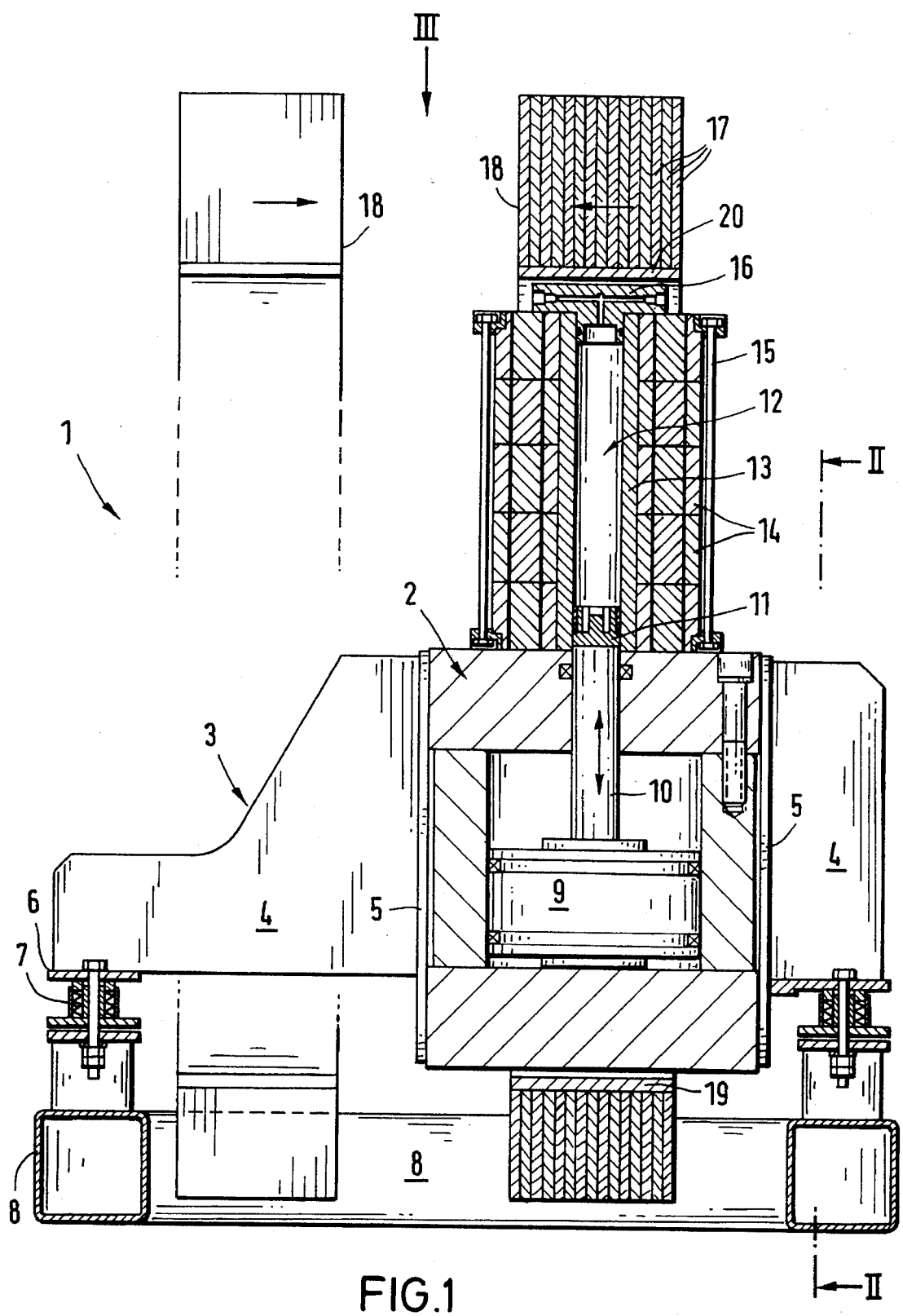
FIG. 1 shows a side partially cross-sectional view of an apparatus according to the present invention with the cylinders being closed.

The apparatus 1 according to the present invention has a low-pressure chamber 2, which is supported in a frame 3. The frame 3 is formed by supporting plates 4 and 5 arranged on cross-members which, in turn, are attached to a base frame 8 by spring elements 7.

A low-pressure piston 9 of low-pressure chamber 2 is displaced by a tandem piston rod 10 and is coupled to a high-pressure piston 11 which generates the pressure required for a high-pressure chamber 12.

The high-pressure chamber 12 is formed of a plurality of cylindrical sections, as shown in FIG. 1. The high pressure chamber 12 includes an inner liner 13 which, as a rule, is compatible with food. The cylindrical sections are embraced by a number of ring members 14 formed of a metal tape. The package, consisting of the cylindrical sections is tensioned by tie rods 15.

The upper end of high-pressure chamber 12 is sealed with a cover 16 which can be lifted and replaced by an automatic device (not shown in the drawings).

Figure 2:
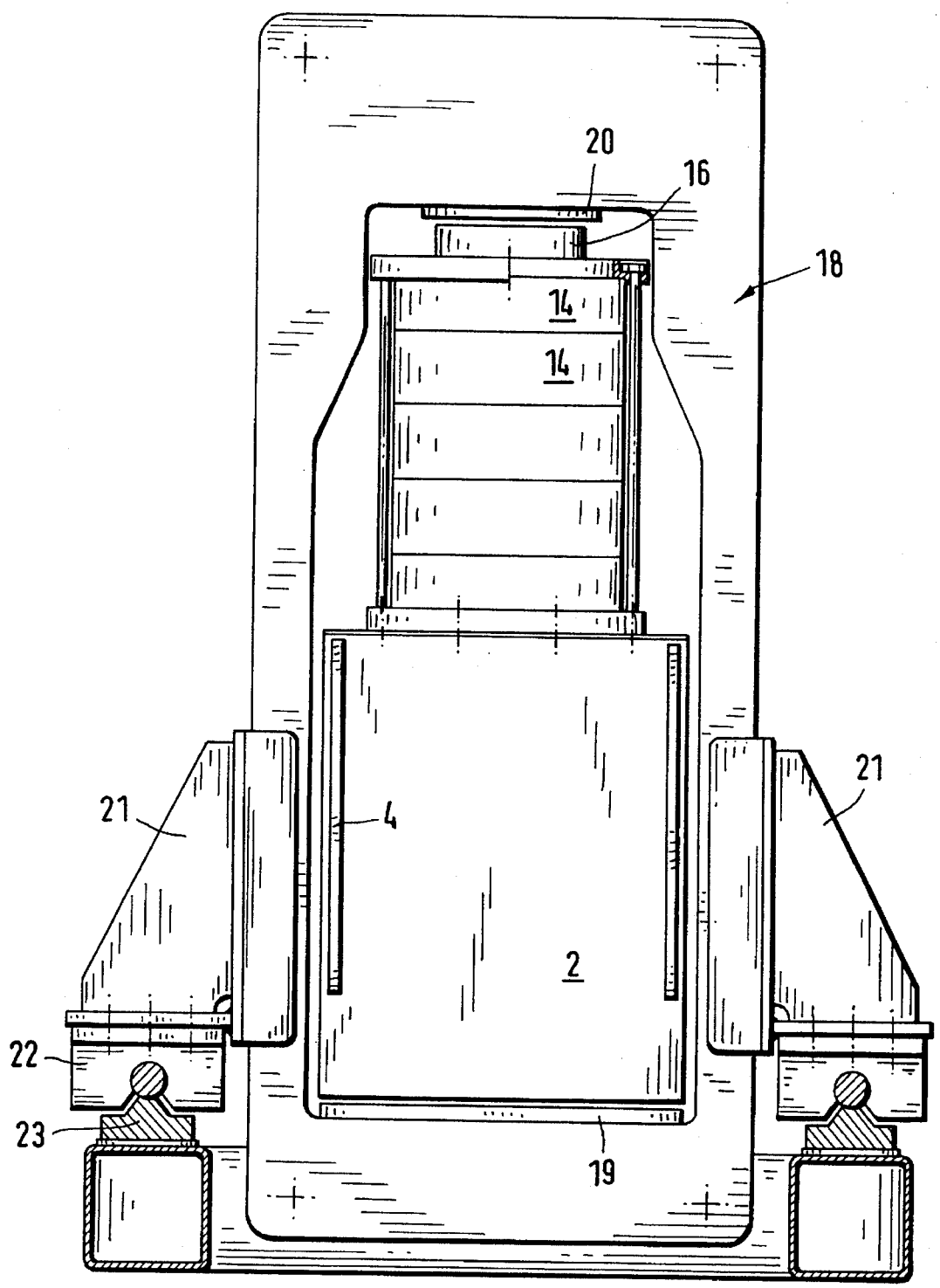
FIG. 2 shows a cross-sectional view along line II—II view FIG. 1.

As shown in FIGS. 1 and 2, the low-pressure chamber 2 and the high-pressure chamber 12 are embraced by a mobile yoke 18 consisting of a plurality of plates 17, the arrangement being such that the lower end plate 19 attached to the yoke 18 can press against the bottom of the low-pressure chamber 2, and an upper cover plate 20 can press against the cover 16 of the high-pressure chamber 12 when the pressure is raised in the pressure chambers and the latter are inclined to expand.

The assembled elements are tensioned by the yoke, i.e. the yoke plates 17 in combination with the bottom plate 19 and the cover plate 20, resulting in that the axial forces are no longer absorbed by the walls of the pressure chambers, but mainly by the yoke plates 17.

Figure 3:
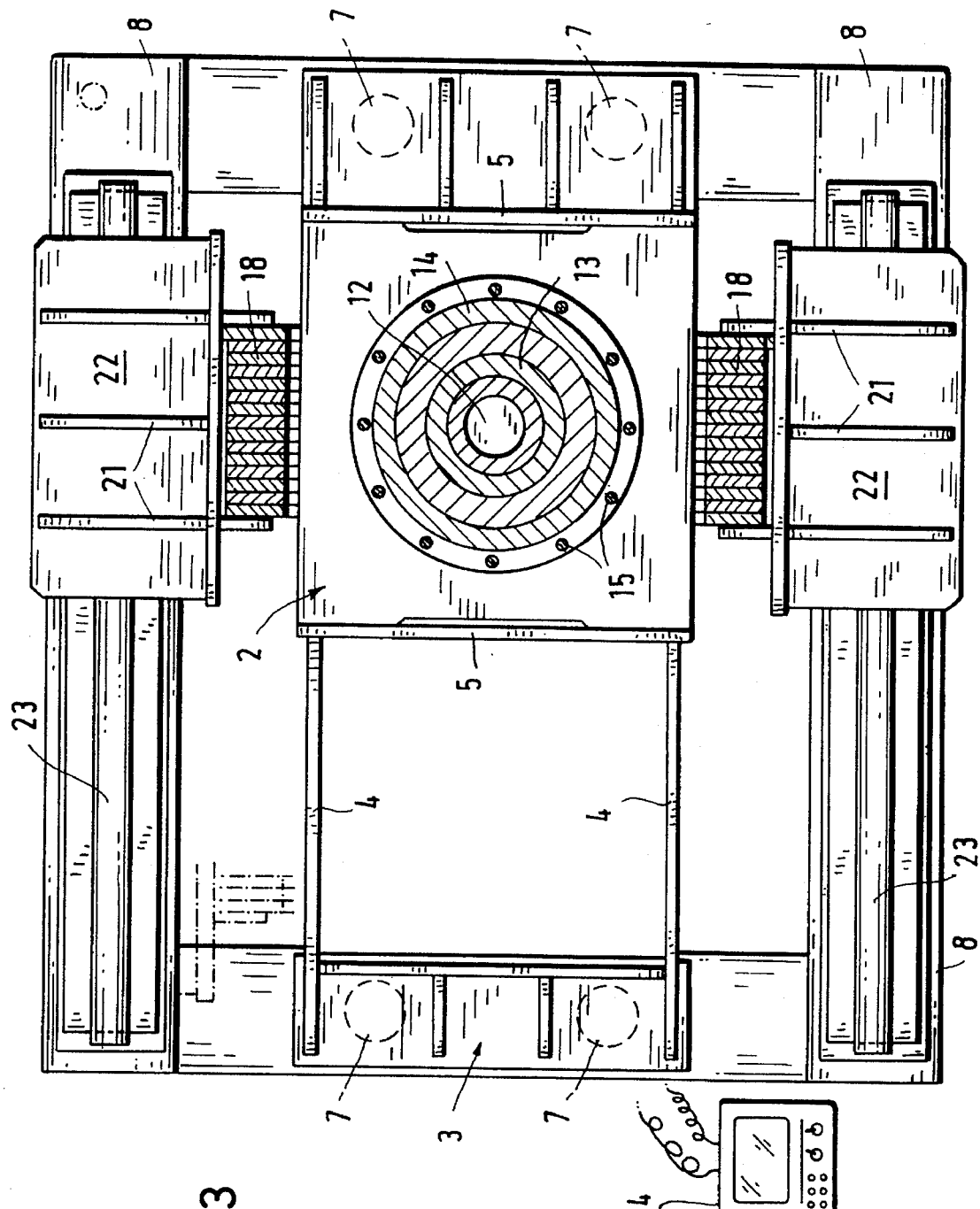
FIG. 3 shows a plan view of the device seen in the direction of arrow III in FIG. I.

A special feature shown in FIGS. 2 and 3 is that the yoke 18 is movable by lateral brackets 21 and corresponding slides 22 placed on rails 23. The small arrows in the upper part of FIG. 1 indicate the travel motion.

FIG. 3 shows a programmable control unit 24 for automatization of the operation of the apparatus and, in particular, the yoke travel and the handling of the upper cover 16.

It goes without saying that the configuration described as an example can be modified in many respects without deviating the basic concept. It would be possible to provide a number of devices operating in cycles with yoke elements lined up in series in order to achieve a high throughput with the aid of a plurality of high-pressure and low-pressure chambers connected in series.

What is claimed is:

1. An apparatus for generating pressure, comprising:

a first chamber having a first diameter;

a second chamber located beneath the first chamber in a direction of action of gravity forces and having a second diameter substantially larger than the first diameter;

a tandem piston for generating pressure in the first and second chambers and having a first portion displaceable in the first chamber and a second substantially larger portion displaceable in the second chamber, the first portion providing an operating pressure in the first chamber;

a cover for closing the first chamber; and a displaceable yoke embracing the first chamber and the second chamber and engaging the cover of the first chamber and a bottom of the second chamber, the yoke applying a pressure fore to the cover of the first chamber and the bottom of the second chamber upon built-up of the operating pressure.

2. An apparatus as set forth in claim 1, further comprising a base frame, and spring supports for supporting the second chamber on the base frame.

3. An apparatus as set forth in claim 1, further comprising rail means mounted on the base frame for displaceably supporting the yoke.

4. An apparatus as set forth in claim 1, wherein the yoke is formed of a stack of plates.

5. An apparatus as set forth in claim 1, wherein the first chamber is formed of a plurality of cylindrical sections and an inner liner, and wherein the apparatus further comprises a plurality of ring members formed of a metal tape for embracing the cylindrical sections.

* * * * *